United States Patent

Saito et al.

[11] Patent Number: 5,872,273
[45] Date of Patent: Feb. 16, 1999

[54] CHIRAL DIPHOSPHINE COMPOUND INTERMEDIATE FOR PREPARING THE SAME TRANSITION METAL COMPLEX HAVING THE SAME DIPHOSPHINE COMPOUND AS LIGAND AND ASYMMETRIC HYDROGENATION CATALYST

[75] Inventors: Takao Saito; Tohru Yokozawa; Xiaoyaong Zhang; Noburo Sayo, all of Hiratsuka, Japan

[73] Assignee: Takasago International Corporation, Tokyo, Japan

[21] Appl. No.: 996,405

[22] Filed: Dec. 22, 1997

[30] Foreign Application Priority Data

Dec. 26, 1996 [JP] Japan .................................. 8-359818

[51] Int. Cl.$^6$ .............................. C07F 9/28; C07F 15/00; C07D 317/06
[52] U.S. Cl. .............................. 556/21; 502/166; 556/13; 556/23; 556/136; 556/138; 568/12; 568/14; 568/17; 549/212; 549/220; 549/221
[58] Field of Search .................................. 568/12, 14, 17; 556/21, 23, 13, 136, 138; 502/166; 549/212, 220, 221

[56] References Cited

U.S. PATENT DOCUMENTS

| | | | |
|---|---|---|---|
| 5,510,503 | 4/1996 | Laue et al. | 556/21 |
| 5,621,128 | 4/1997 | Jendralla | 556/18 |
| 5,631,393 | 5/1997 | Kohlpaintner et al. | 556/17 |

*Primary Examiner*—Porfirio Nazario-Gonzalez
*Attorney, Agent, or Firm*—Kubovcik & Kubovcik

[57] ABSTRACT

A novel diphosphine compound of the formula (I):

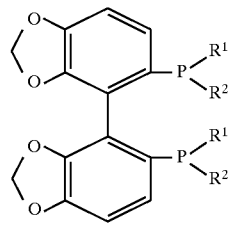

where $R^1$ and $R^2$ represent independently cycloalkyl, unsubstituted or substituted phenyl, or a five-membered heteroaromatic ring. The compound is useful as a ligand for an asymmetric reaction, in particular, as an asymmetric hydrogenation catalyst.

7 Claims, No Drawings

CHIRAL DIPHOSPHINE COMPOUND INTERMEDIATE FOR PREPARING THE SAME TRANSITION METAL COMPLEX HAVING THE SAME DIPHOSPHINE COMPOUND AS LIGAND AND ASYMMETRIC HYDROGENATION CATALYST

BACKGROUND OF THE INVENTION

1. Field of the Invention

The present invention relates to a novel optically active diphosphine compound, an intermediate for preparing the same, a transition metal complex having the same diphosphine compound as a ligand and a transition metal catalyst useful for a variety of asymmetric synthetic reactions.

2. Description of the Related art

There have hitherto been many reports on transition metal complexes which can be utilized for asymmetric syntheses such as asymmetric hydrogenation reactions, asymmetric isomerization reactions, asymmetric hydrosilylation reactions and the like. Inter alia, complexes in which transition metal complexes such as ruthenium, rhodium, iridium, palladium and the like are coordinated with an optically active tertiary phosphine compound have potent performance as a catalyst for an asymmetric reaction.

In order to further enhance performance, many phosphine compounds having various structures have hitherto been developed (Kagakusosetsu 32, edit. by Nippon Chemistry Society, "Chemistry of Organometallic Complexes", 237–238 (1982); "Asymmetric Catalysis in Organic Synthesis", Ryoji Noyori, A Wiley-Interscience Publication).

Inter alia, 2,2'-bis(diphenylphosphino)-1,1'-binaphthyl (hereinafter referred to "BINAP") is one of the excellent optically active phosphines, and a rhodium complex having the BINAP as a ligand (JP-A 55-61973) and a ruthenium complex (JP-A 61-63690) have been previously reported.

Further, it has been reported that a rhodium complex (JP-A No. 60-199898) and a ruthenium complex (JP-A 61-63690) having 2,2'-bis(di-(p-tolyl)phosphino)-1,1'-binaphthyl (hereinafter referred to as "p-TolBINAP") as a ligand give better results in an asymmetric isomerization reaction. Further, it has been reported in JP-A No. 3-255090 that a ruthenium complex of 2,2'-bis(di-(3,5-dialkylphenyl) phosphino)-1,1'-binaphthyl gives better results in a reaction for the asymmetric hydrogenation of β-ketoesters.

However, selectivities (diastereoselectivity, enantioselectivity) and catalytic activity are not sufficient depending upon an objective reaction and reaction substrate and, thus, improvement in a catalyst is occasionally demanded.

SUMMARY OF THE INVENTION

Accordingly, an object of the present invention is to provide a novel phosphine compound having excellent performance (diastereoselectivity, enantioselectivity, catalytic activity) as a catalyst for an asymmetric reaction, in particular, an asymmetric hydrogenation reaction.

Especially, a transition metal complex including optically active ((5,6),(5',6')-bis(methylenedioxy)biphenyl-2,2'-diyl) bis(diphenylphosphine) (hereinafter referred to as "SEGPHOS" in some cases) is effective for an asymmetric hydrogenation reaction.

Another object of the present inventions is to provide a catalyst comprising the phosphine compound and a transition metal selected from Ru, Ir, Pd, Rh or Ni.

PREFERRED EMBODIMENTS OF THE INVENTION

The present invention will be described in detail below.

One of the diphosphine compounds of the present invention is represented by the following formula (1):

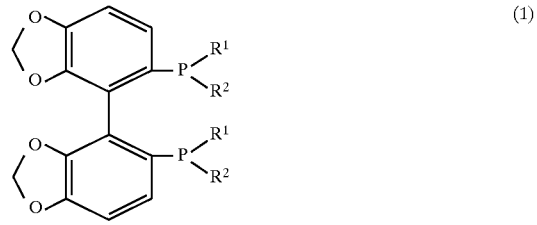

where $R^1$ and $R^2$ independently represent cycloalkyl, unsubstituted or substituted phenyl, or a five-membered heteroaromatic ring residue.

The cycloalkyl as $R^1$ and $R^2$ is cyclopentyl, cyclohexyl or cycloheptyl. The five-membered heteroaromatic ring as $R^1$ and $R^2$ is 2-furyl, 3-furyl, 2-benzofuryl or 3-benzofuryl. Examples of substituents in the substituted phenyl are $C_1$–$C_4$ alkyl, $C_1$–$C_4$ alkoxy, di-(lower alkyl)amino or halogen. As used herein, lower alkyl is alkyl having 1 to 5 carbon atoms.

Among the aforementioned compounds, preferable compounds are represented by the formula (5):

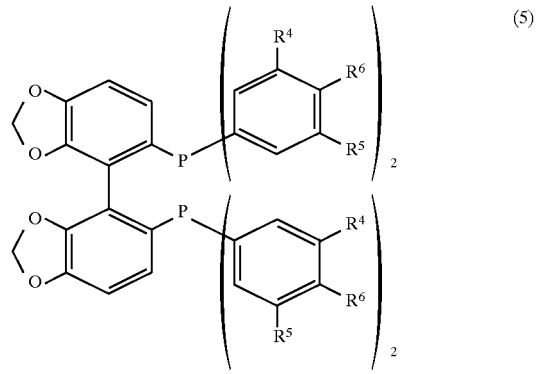

where $R^4$ and $R^5$ independently represent hydrogen, $C_1$–$C_4$ alkyl, $C_1$–$C_4$ alkoxy; $R^6$ represents hydrogen, $C_1$–$C_4$ alkyl, $C_1$–$C_4$ alkoxy or di ($C_1$–$C_4$ alkyl)-amino, and more preferable compounds are represented by the formula (6):

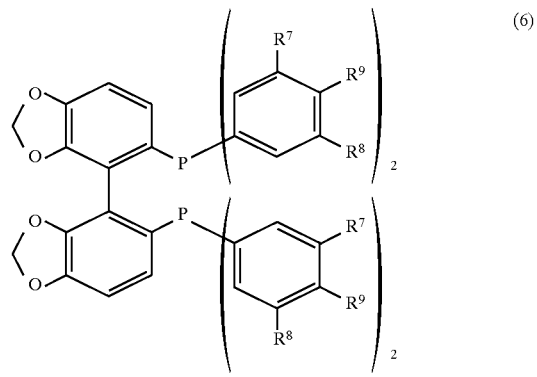

where $R^7$ and $R^8$ are the same or different and represent hydrogen, t-butyl, n-butyl, n-propyl, isopropyl, ethyl or methyl; $R^9$ represents hydrogen, t-butoxy, isopropoxy, ethoxy or methoxy.

Another compound of the present invention is represented by the following formula (2):

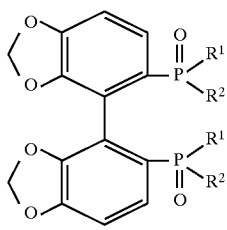

(2)

where R[1] and R[2] are as defined above.

The compound of the formula (2) is an intermediate for preparing the compounds of the aforementioned formula (1).

The present invention includes racemic compounds and optically active compounds of the aforementioned compounds.

Another diphosphine compound of the present invention is represented by the following formula (3):

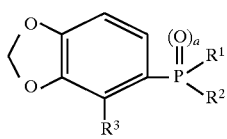

(3)

where R[1] and R[2] are the same as defined above.

The compound of the formula (3) is an intermediate for preparing the compound of the aforementioned formula (2).

A process for preparing these compounds will be described below.

In order to avoid complexity, a representative embodiment of a process for preparing the present compounds is explained by referring to a compound of the following formula(7); (−)-((5,6),(5',6')-bis(methylenedioxy)biphenyl-2,2'-diyl)bis(diphenylphosphine) (hereinafter referred to as "(−)-SEGPHOS in some cases) among the compounds included in the present invention. However, the present invention is not limited thereto.

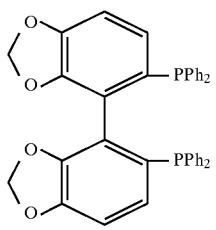

(7)

Magnesium and 3,4-methylenedioxybromobenzene (8) are reacted to obtain a Grignard reagent, on which is acted diphenylphosphinyl chloride to obtain diphenyl(3,4-methylenedioxyphenyl)phosphine oxide (3a) (R[1] and R[2]=Ph, R[3]=H, a=1).

The compound (3a) can be reduced by a known method to obtain diphenyl(3,4-methylenedioxyphenyl)phosphine.

(3a) and iodine are reacted in the presence of lithium diisopropylamide to obtain an iodocompound (3b).

Then, the iodocompound (3b) is heated in dimethylformamide (hereinafter referred to as "DMF") in the presence of copper powder to obtain racemic diphosphine oxide (9) (R[1] and R[2]=Ph)

The racemic phosphine oxide can be resolved with (−)-L-dibenzoyltartaric acid by forming a crystalline equimolar complex. Reduction of the resolved phosphine oxide with trichlorosilane gives (−)-SEGPHOS in good yield.

In addition, (+)-SEGPHOS can be obtained by optical resolution using (+)-D-benzoyltartaric acid.

Further, the present diphosphine compound having a substituent in the phenyl ring can be prepared by using a diarylphosphinyl chloride having a substituent on its phenyl ring in place of the diphenylphosphinyl chloride.

(Scheme 1)

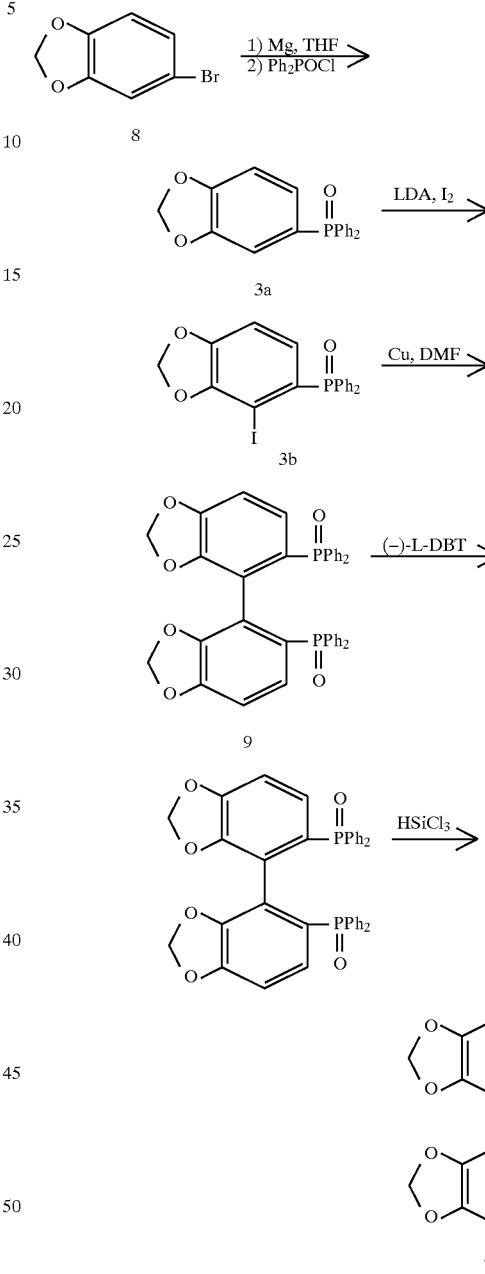

The compound (2) (R[1] and R[2]=Ph) which is optically active among the present compounds can also be obtained by resolving and reducing enantiomers by liquid chromatography using an optically active column.

Among the present compounds, inter alia, the optically active compound (1) is useful as a ligand for a transition metal complex catalyzed asymmetric reaction. In addition, among the present compounds (1), the racemic one is also useful as an intermediate for preparing the optically active compounds (1).

Examples of the transition metal include rhodium, ruthenium, iridium, palladium, nickel and the like.

The transition metal complexes can be prepared by the known methods.

Here, with respect to symbols used in the formulas of the transition metal complexes described below, L represents the optically active compounds among the present invention, cod represents 1,5-cyclooctadiene, nbd represents norbornadiene, Ph represents phenyl group, and Ac represents acetyl group.

Rhodium complex:

Specifically, a rhodium complex can be prepared, for example, by reaction of bis(cycloocta-1,5-diene)rhodium (I) tetrafluoroborate with the present SEGPHOS according to a method described in "Experimental Chemistry, 4th edition", volume 18, Organometallic Complexes, pp.339–344, Ed. Chemical Society of Japan, 1991, published by Maruzen. Examples of the rhodium compound include the following:
[Rh(L)Cl]$_2$, [Rh(L)Br]$_2$, [Rh(L)I]$_2$,
[Rh(cod)(L)]BF$_4$, [Rh(cod)(L)]BPh$_4$,
h(cod)(L), [Rh(cod)(L)]BPh$_4$,
[Rh(nbd)(L)]BF$_4$, [Rh(nbd)(L)]ClO$_4$,
[Rh(nbd)(L)]PF$_6$, [Rh(nbd)(L)]Bph$_4$ Ruthenium complex:

A ruthenium complex can be prepared by heating [Ru(cod)Cl$_2$]n and SEGPHOS at reflux with toluene in the presence of triethylamine as described in the literature (T. Ikariya, Y. Ishii, H. Kawano, T. Arai, M. Saburi, S. Yoshikawa, and S. Akutagawa, J. Chem. Soc., Chem. Commun., 922 (1988)). Alternatively, the ruthenium complex can be obtained by heating [Ru(p-cymene)I$_2$]$_2$ and SEGPHOS in methylene chloride and ethanol under stirring according to a method described in the literature (K. Mashima, K. Kusano, T. Ohta, R. Noyori, H. Takaya, J. Chem. Soc., Chem. Commun., 1208 (1989)). Examples of the ruthenium complex are as follows:
Ru(OAc)$_2$(L)Ru$_2$Cl$_4$(L)$_2$NEt$_3$
[RuCl(benzene)(L)], [RuBr(benzene)(L)]Br, [RuI(benzene)(L)]I,
[RuCl(p-cymene)(L)]Cl, [RuBr(p-cymene)(L)]Br, [RuI(p-cymene)(L)]I,
[Ru(L)](Bf$_4$)2, [Ru(L)](ClO$_4$)$_2$, [Ru(L)](PF$_6$)$_2$, [Ru(L)](BPh$_4$)$_2$ Iridium complex An iridium complex can be prepared by reaction of SEGPHOS with [Ir(cod)(CH$_3$CN)$_2$]BF$_4$ in tetrahydrofuran under stirring according to a method described in the literature (K. Mashima, T. Akutagawa, X. Zhang, T. Taketomi, H. Kumobayashi, S. Akutagawa, J. Organomet., Chem. 1992, 428, 213). Examples of the iridium complex are as follows:
[Ir(L)Cl]$_2$, [Ir(L)Br]2$_1$, [Ir(L)I]$_2$,
[Ir(cod)(L)]BF$_4$, [Ir(cod)(L)]ClO$_4$,
[Ir(cod)(L)]PF$_6$, [Ir(cod)(L)]BPh$_4$,
[Ir(nbd)(L)]BF$_4$, [Ir(nbd)(L)]Cl$_4$
[Ir(nbd)(L)]PF$_6$, [Ir(nbd)(L)]BPh$_4$ Palladium complex A palladium complex can be prepared by reaction of SEGPHOS with π-allylpalladium chloride according to a method described in the literature (Y, Uozumi and T, Hayashi, J. Am. Chem. Soc., 1991, 113, 9887). Examples of the palladium complex are as follows:
PdCl$_2$(L), (π-allyl)Pd(L),
[Pd(L)]BF$_4$, [Pd(L)]ClO$_4$, [Pd(L)]PF$_6$, [Pd(L)]BPh$_4$ Nickel complex:

A nickel complex can be prepared according to a method described in, for example, "Experimental Chemistry, 4th edition" vol. 18, Organometallic complexes, p. 376, Ed. Chemical Society of Japan, 1991, published by Maruzen, or alternatively, can be prepared by dissolving SEGPHOS and nickel chloride with a mixed solvent of isopropanol and methanol, followed by heating under stirring according to a method described in the literature (Y. Uozumi and T, Hayashi, J. Am. Chem. Soc., 1991, 113, 9887).

Examples of the nickel complex are as follows:
NiCl$_2$(L), NiBr$_2$(L), NiI$_2$(L)

The transition metal complexes having this novel optically active diphosphine compound as a ligand are useful as a catalyst for an asymmetric hydrogenation reaction. Upon the use of the complex as a catalyst, the complex may be used after enhancing the purity thereof or without purification thereof.

Among the aforementioned transition metal complexes, in particular, a complex containing ruthenium and SEGPHOS which is an optically active diphosphine compound gives higher enantioselectivity in the asymmetric hydrogenation of 2-oxo-1-propanol than ruthenium complexes having the ligand such as BINAP, p-TolBINAP and the like. In addition, a complex containing ruthenium and ((5,6),(5',6')-bis(methylendioxy)biphenyl-2,2'-diyl)bis((bis-3,5-dimethylphenyl)phosphine)(hereinafter referred to as "DM-SEGPHOS") as a ligand gives the equivalent enantioselectivity to that of ruthenium complexes of BINAP, p-TolBINAP and the like in a reaction for asymmetric hydrogenation of methyl 2-benzamidomethyl-3-oxybutyrate and gives higher diastereoselectivity and catalytic activity.

Thus, the novel diphosphine compounds of the present invention are useful as, in particular, a ligand for a transition metal complex. In addition, the transition metal complexes are useful catalyst for asymmetric reaction and are extremely industrially useful.

The following Examples and Use Examples further illustrate the present invention in detail but are not to be construed to limit the scope thereof.

EXAMPLES

Apparatuses used for determining physical properties in respective Examples are as follows:

Nuclear magnetic resonance: $^1$H NMR Bruker AM400 (400MHz) $^{31}$P NMR Bruker AM400 (162MHz)

Melting point: Yanaco MP-500D

Optical rotation: Nihon Bunkoh Co., Ltd. DIP-4

Gas chromatography GLC: Hewlett Packard 5890-11

High-performance liquid chromatography HPLC: LC10AT & SPD10A manufactured by Shimadzu Corporation Mass spectrometry (MASS): M-80B manufactured by Hitachi

Example 1

Synthesis of diphenyl((3,4)-methylenedioxyphenyl)phosphine oxide

Magnesium (12.4 g, 511 mmol) was charged into a four-necked round-bottomed flask, equipped with a thermometer, a condenser and a pressure equalizing dropping funnel, and the air inside the flask was completely replaced with nitrogen, and 30 ml of anhydrous tetrahydrofuran was added thereto. To this solution was added a 200 ml solution of 4-bromo-1,2-methylenedioxybenzene (93.6 g, 465 mmol) (manufactured by Tokyokasei) in tetrahydrofuran (hereinafter referred to as "THF") dropwise over 2.5 hours under water-cooling and stirring was further continued at room temperature for 3 hours. To the resulting mixture was added 100 g (423 mmol) of diphenyl phosphinyl chloride dropwise over 2 hours under ice-cooling and stirring was continued at room temperature for 15 hours. Thereafter, 30 ml of water was added thereto under ice-cooling to stir for 30 minutes, then 150 ml of 1N hydrochloric acid was added thereto, followed by stirring for 1.5 hours. The reaction product was extracted with 300 ml of ethyl acetate, washed successively with 150 ml of 1N hydrochloric acid, 150 ml of an aqueous saturated sodium bicarbonate and 150 ml of water, and the solvent was distilled off under reduced pressure.

The resulting crystals was dissolved in 150 ml of toluene under heating, followed by recrystallization at −5° C. to obtain 127 g of the titled compound.

mp : 127°–128° C.

$^1$H-NMR(CDCl$_3$) : δ 6.01(2H,S), 6.88(1H,dd,J=10.3,2.4 Hz), 7.08(1H,dd,J=10.0 Hz), 7.18(1H,ddd,J=13.5,10.3, 2.4 Hz), 7.43–7.48(4H,m), 7.51(2H,m), 7.64–7.70(4H, m)

$^{31}$P-NMR(CDCl$_3$) : δ29.8.

Example 2

Synthesis of diphenyl(2-iodo-(3,4)-methylenedioxyphenyl) phosphine oxide 20.0 g (62.1 mmol) of diphenyl((3,4)-methylenedioxyphenyl)phosphine oxide was dissolved in 250 ml of THF under a nitrogen stream. To this solution was added 93 ml of a solution of lithiumdiisopropylamide in THF (0.7M) dropwise at −78° C. over 30 minutes, and stirring was continued at the same temperature for 1.5 hours. The resulting mixture was added dropwise to a solution of 16.5 g (65.2 mmol) of iodine in 50 ml of THF at −78° C. for 30 minutes and, thereafter, a temperature was raised to 0° C., followed by stirring for 1 hour. After THF was distilled off, the residue was dissolved in 500 ml of ethyl acetate, washed successively with 500 ml of an aqueous saturated ammonium chloride and 300 ml of a saturated sodium chloride and dried over anhydrous magnesium sulfate. After the solvent was distilled off, the residue was purified by silica gel column chromatography (eluent hexane:ethyl acetate=2:5) to obtain 22.2 g of the titled compound.

mp : 191°–193° C.

$^1$H-NMR)CDCl$_3$) : δ6.08(2H,s), 6.68(1H,dd,J=8.0,2.2 Hz), 6.74(2H,dd,J=13.3, 8.0 Hz) 7.47–7.49(4H,m), 7.54(2H,dd,J=7.5, 1.6 Hz), 7.68–7.73(4H,m)

$^{31}$P-NMR(CDCl$_3$) : δ29.8.

Example 3

Synthesis of (±)-((5,6),(5',6')-bis(methylenedioxy)biphenyl-2,2'-diyl)bis(diphenylphosphine oxide)

A mixture of 58.40 g (0.130 ml) of the iodide obtained in Example 2, 24.85 g (0.390 mol) of copper powders and 228 ml of DMF was heated at a bath temperature of 140° C. for 8 hours under stirring. The reaction mixture was filtered with a pad of celite and the solvent was distilled off under reduced pressure. The residue was dissolved in 900 ml of methylene chloride, washed with 500 ml of an aqueous saturated ammonium chloride and 300 ml of saturated sodium chloride and dried over anhydrous magnesium sulfate. The solvent was distilled off under reduced pressure and the residue was purified by silica gel column chromatography. The resultant solid was recrystallized from a mixed solvent of 45 ml of ethyl acetate and 5 ml of hexane to obtain 18.5 g of the titled compound. The mother liquor was concentrated and washed with diisopropyl ether to obtain 12.10 g of the titled compound.

mp : 230°–232° C.

$^1$H-NMR(CDCl$_3$) : δ5.26(2H,d,J=1.5 Hz), 5.72(2H,d,J= 1.6 Hz), 6.65(2H,dd,J=8.1,2.1 Hz) 6.77(2H,dd,J=14.1, 8.1 Hz),7.28–7.72(20H,m)

$^{31}$P-NMR(CDCl$_3$) : δ−12.6

EI-MS m/z 642(M$^+$)

Example 4

Optical resolution of (±)-((5,6),(5',6')-bis(methylenedioxy) biphenyl-2,2'-diyl)bis(diphenylphosphine oxide)

A solution of 12.07 g (18.8 mmol) of (±)-((5,6),(5',6')-bis (methylenedioxy)biphenyl-2,2'-diyl)bis(diphenylphosphine oxide)(hereinafter referred to as (±) -SEGPHOSO$_2$ in some cases) in 60 ml of chloroform was refluxed. A solution of 7.43 g (19.7 mmol) of (−)-dibenzoyl-L-tartaric acid in 20 ml of ethyl acetate was added dropwise thereto. After stirring for 30 minutes, the solvent was distilled off under reduced pressure. The residue was dissolved in 110 ml of ethyl acetate, which was heated to 60° C. and 40 ml of carbon tetrachloride was added thereto. Upon cooling to room temperature, 5.51 g of precipitated solid was obtained by filtration. The solid was washed with a mixed solvent of 40 ml of ethyl acetate, 10 ml of carbon tetrachloride and 2 ml of ethanol to give 4.53 g of white solid. The solid was dissolved in 40 ml of chloroform, and 20 ml of 1N aqueous sodium hydroxide was added thereto, followed by stirring at room temperature for 1 hour. The organic layer was separated, washed successively with water and an aqueous sodium chloride solution and dried over anhydrous sodium sulfate.

The solvent was distilled off under reduced pressure, the residue was dissolved in 30 ml of chloroform, and then 1.70 g (4.51 mmol) of (−)-dibenzoyl-L-tartaric acid was added and the mixture refluxed for 30 minutes and cooled to room temperature. The precipitate (2.77 g) was dissolved in chloroform, and 1N aqueous sodium hydroxide solution was added, followed by stirring at room temperature for 1 hour. The organic layer was separated, washed successively with water and an aqueous sodium chloride solution and dried over anhydrous sodium sulfate. The solvent was distilled off under reduced pressure to obtain 1.91 g of (−)-((5,6),(5',6') -bis(methylenedioxy)biphenyl-2,2'-diyl)bis (diphenylphosphine oxide)(hereinafter referred to as "(−)-SEGPHOSO$_2$) with 100% ee. [α]$_D^{24}$ −161.9°(c0.063, CHCl$_3$)

Example 5

Synthesis of (−)-((5,6),(5',6')-bis(methylenedioxy)biphenyl-2,2'-diyl)bis(diphenylphosphine): (−)-SEGPHOS Trichlorosilane (3.22 g, 23.3 mmol) was added dropwise to 1.50 g (2.34 mmol) of (−)-SEGPHOSO$_2$, 3.11 g (25.6 mmol) of dimethylaniline and 25 ml of toluene, followed by stirring at 100 ° C. for 4 hours. The reaction mixture was ice-cooled and 30 ml of 4N aqueous sodium hydroxide solution was added thereto, followed by stirring at room temperature for 30 minutes. After the aqueous layer was separated, the reaction product in the aqueous layer was extracted twice with 15 ml of toluene. A combined solution of the organic layer and the toluene was washed successively twice with 30 ml of hydrochloric acid and water, and 30 ml of an aqueous sodium chloride solution. After drying over anhydrous magnesium sulfate, the solvent was distilled off under reduced pressure and the residue was purified by silica gel column chromatography to obtain 1.21 g (yield 85%) of the titled compound as a colorless solid.

mp : 215°–217° C.

$^1$H-NMR(CDCl$_3$) : δ5.03(2H,d,J=1.6 Hz), 5.66(2H,d,J= 1.6 Hz), 6.51(2H,dd,J=7.9,3.1 Hz), 6.66(2H,d,J=8.1 Hz), 7.11–7.21(20H,m)

Example 6
Preparation of [RuCl(benzene)((−)-SEGPHOS]Cl

A mixture of [Ru(benzene)Cl$_2$]$_2$ (20.5 mg, 0.041 mmol), (S)-(−)-SEGPHOS (50 mg, 0.081 mmol), 3 ml of methylene chloride and 3 ml of ethanol was stirred in 20 ml of a schlenk tube at 50° C. for 3 hours. The solvent was distilled off, followed by vacuum-drying to give 69.3 mg of the titled compound.

$^{31}$P-NMR(CDCl$_3$) δ27.0(d,J=62.4 Hz), 41.9(d,J=62.1 Hz)

Example 7
Synthesis of bis((3,5)-dimethylphenyl)((3,4)-methylenedioxyphenyl)phosphine oxide Magnesium (4.2 g, 171 mmol) was charged into a four-neck round-bottomed flask equipped with a thermometer, a condenser and a pressure equalizing dropping funnel, and the air inside the flask was completely replaced with nitrogen, and 10 ml of anhydrous tetrahydrofuran was added thereto. To this solution was added a solution of 4-bromo-1,2-methylenedioxybenzene (34.4 g, 171 mmol) in 70 ml of THF dropwise over 2.5 hours with water-cooling stirring and successively stirring was further continued at room temperature for 3 hours. To the resulting mixture was added 50 g (171 mmol) of bis((3,5)-dimethylphenyl) phosphinyl chloride in 100 ml of THF dropwise over 1 hours with water-cooling stirring and stirring was continued at room temperature for 15 hours. Thereafter, 10 ml of water was added thereto with ice-cooling to stir for 30 minutes, then 100 ml of 1N hydrochloric acid was added thereto, followed by stirring for 1.5 hours. The product was extracted with 150 ml of ethyl acetate, washed successively with 100 ml of 1N hydrochloric acid, 100 ml of an aqueous saturated sodium bicarbonate solution and 100 ml of water, and the solvent was distilled off under reduced pressure. The residue was purified by silica gel column chromatography (eluent; hexane:ethyl acetate=1:1) to give 60.0 g of the titled compound.

mp : 154°–155° C.

$^1$H-NMR(CDCl$_3$) : δ2.32(12H,s), 6.02(2H,s), 6.88(1H, dd,J=7.9, 2.3 Hz), 7.07(1H,dd,J-11.3, 1.4 Hz), 7.19(2H, bs), 7.20–7.21(1H,m), 7.25–7.28(4H,m)

$^{31}$P-NMR(CDCl$_3$) : δ30.3

Example 8
Synthesis of bis((3,5)-dimethylphenyl)(2-iodo-(3,4)-methylenedioxyphenyl)phosphine oxide Bis((3,5)-dimethylphenyl)((3,4)-methylenedioxyphenyl) phosphine oxide (60.0 g, 158.7 mmol) was dissolved in 330 ml of THF under a nitrogen stream. To this solution was added 250 ml of a solution of lithiumdiisopropylamide in THF (0.7M) dropwise at −78° C. over 20 minutes and a temperature was raised to −40° C. The resulting mixture was cooled to −78° C., a solution of 44.6 g (175.7 mmol) of iodine in 160 ml of THF was added dropwise over 20 minutes and, thereafter, a reaction temperature was raised to 0° C., followed by further stirring for 1 hour. After THF was distilled off, the residue was dissolved with 500 ml of ethyl acetate, washed with 500 ml of an aqueous ammonium chloride solution and 300 ml of a saturated sodium chloride solution and dried over anhydrous magnesium sulfate. The solvent was distilled off under reduced pressure, and the residue was purified by silica gel column chromatography (eluents; hexane:ethyl acetate=2:5) to obtain 58.9 g of the titled compound.

mp : 229°–236° C.

$^1$H-NMR(CDCl$_3$) : δ2.34(12H,bs), 6.10(2H,s), 6.68(1H, dd,J=7.9,2.5 Hz), 6.71(1H,dd,J=20.8,8.0 Hz) 7.17(2H, m), 7.27–7.31(4H,m)

$^{31}$P-NMR(CDCl$_3$) : δ33.9

Example 9
Synthesis of (±)-((5,6),(5',6')-bis(methylenedioxy)biphenyl-2,2'-diyl)bis(bis(3,5-dimethylphenyl)phosphine oxide): (±)-DM-SEGPHOSO$_2$ A mixture of the iodide (54.0 g, 107.2 mol) obtained in Example 8, 20.4 g (321.5 mmol) of copper powders and 210 ml of DMF was heated with stirring at 140° C. for 3 hours under a nitrogen stream. The reaction mixture was filtered with a pad of celite and the solvent was distilled off under reduced pressure. The residue was dissolved in 500 ml of methylene chloride, washed successively with 500 ml of an aqueous ammonium chloride solution and 300 ml of a saturated sodium chloride solution and dried over anhydrous magnesium sulfate. After the solvent was distilled off under reduced pressure, 500 ml of hexane was added to precipitate the crystals. The crystals were collected by filtration, and which was washed with 300 ml of 99.5% ethanol to give 32.0 g of the titled compound.

mp : 256°–258° C.

$^1$H-NMR(CDCl$_3$) : δ2.11(12H,s),2.30(12H,s), 5.43(2H,d, J=1.6 Hz), 5.77(2H,d,J=1.6 Hz), 6.65(2H,dd,J=8.1,2.0 Hz) 6.92(2H,dd,J=14.0,8.1 Hz), 6.95(2H,s), 7.09(2H, s), 7.14(4H,d,J=12.2 Hz), 7.37(4H,d,J=12.1 Hz)

$^{31}$P-NMR(CDCl$_3$) : δ30.5

EI-MS m/z 754(M$^+$)

Example 10
Optical resolution of (±)-((5,6),(5',6')-bis(methylenedioxy) biphenyl-2,2'-diyl)bis(bis(3,5-dimethylphenyl)phosphine oxide): DM-SEGPHOSO$_2$ (±)-DM-SEGPHOSO$_2$ was separated by using CHIRAL-CEL OD (20 mm×250 mm, Eluents: Hexane/2-Propanol=95/5, Flow: 4.0 ml/min.) to obtain (−)-DM SEGPHOSO$_2$.

mp : 256°–258° C.

$[\alpha]_D^{24}$ −161.9°(C 0.063,CHCl$_3$)

Example 11
Synthesis of (−)-((5,6),(5',6')-bis(methylenedioxy)biphenyl-2,2'-diyl)bis(bis(3,5-dimethylphenyl)phosphine oxide): (−)-DM-SEGPHOS Trichlorosilane (187.6 mg, 1.39 mmol) was added dropwise to a mixture of 99.1 mg (0.131 mmol) of (−)-DM-SEGPHOSO$_2$, 191.2 mg (1.58 mmol) of dimethylaniline and 5 ml of toluene, followed by stirring 100° C. for 15 hours. The reaction mixture was ice-cooled, 10 ml of an 1N aqueous sodium hydroxide solution was added thereto, followed by stirring at room temperature for 30 minutes. After the aqueous layer was separated, the aqueous layer was extracted with ethyl acetate, a combined organic layer was washed with 1N hydrochloric acid, water and an aqueous saturated sodium chloride solution. After drying over anhydrous magnesium sulfate, the solvent was distilled off, and the residue was purified by silica gel column chromatography to obtain 49.1 mg (yield 52%) of the titled compound.

Example 12~35
The compounds in the following table were synthesized in an analogous manner to Examples 1 to 5.

| Example | compounds | m.p. (°C.) | $[\alpha]_D^{20}$ | $^{31}$P-NMR (ppm) | optical resolution |
|---|---|---|---|---|---|
| 12 | (±)-DMM-SEGPHOSO$_2$ | 257–258 | — | 29.27(s) | |
| 13 | (+)-DMM-SEGPHOSO$_2$ | 153–156 | +206.5(benzene) | — | (+)-DBT |
| 14 | (−)-DMM-SEGPHOS | 142–144 | 8.2(benzene) | −14.26(s) | |
| 15 | (±)-DTBM-SEGPHOSO$_2$ | 154–157 | — | 30.19(s) | |
| 16 | (+)-DTBM-SEGPHOSO$_2$ | 144–145 | +36.8(CH$_2$Cl$_2$) | — | (−)-DBT |
| 17 | (−)-DTBM-SEGPHOS | 126–128 | 54.1(CH$_2$Cl$_2$) | −12.31(s) | |
| 18 | (±)-DTB-SEGPHOSO$_2$ | 248–250 | — | 31.6(s) | |
| 19 | (−)-DTB-SEGPHOSO$_2$ | 133–134 | −66.7(CH$_2$Cl$_2$) | — | HPLC separation |
| 20 | (+)-DTB-SEGPHOS | 112–113 | +17.6(CH$_2$Cl$_2$) | −10.04(s) | |
| 21 | (±)-T-SEGPHOSO$_2$ | 156–158 | — | −29.6(s) | |
| 22 | (−)-T-SEGPHOSO$_2$ | 168–170 | −163.3(CH$_2$Cl$_3$) | — | (+)-DBT |
| 23 | (−)-T-SEGPHOS | 188–189 | −8.4(CH$_2$Cl$_3$) | −13.84(s) | |
| 24 | (±)-TB-SEGPHOSO | 203–205 | — | 29.49(s) | |
| 25 | (+)-TB-SEGPHOSO$_2$ | 205–208 | +110.2(CH$_2$Cl$_2$) | — | (−)-DBT |
| 26 | (+)-TB-SEGPHOS | 290(dec.) | +0.72(CH$_2$Cl$_2$) | −15.06(s) | |
| 27 | (±)-p-MeO-SEGPHOSO$_2$ | 122–124 | — | 29.46(s) | |
| 28 | (+)-p-MeO-SEGPHOSO$_2$ | 144–146 | +116.4(CH$_2$Cl$_2$) | — | HPLC separation |
| 29 | (−)-p-MeO-SEGPHOS | 245–246 | −3.0(CH$_2$Cl$_2$) | −15.5(s) | |
| 30 | (±)-p-Cl-SEGPHOSO$_2$ | 313(dec.) | — | 28.72(s) | |
| 31 | (+)-p-Cl-SEGPHOSO$_2$ | 163–165 | +102.8(CH$_2$Cl$_2$) | — | HPLC separation |
| 32 | (+)-p-Cl-SEGPHOS | 123–125 | +13.5(CH$_2$Cl$_2$) | −14.44(s) | |
| 33 | (±)-Cy-SEGPHOSO$_2$ | 270(dec.) | — | 46.32(s) | |
| 34 | (−)-Cy-SEGPHOSO$_2$ | 305(dec.) | −24.0(CH$_2$Cl$_2$) | — | (−)-DBT |
| 35 | (+)-Cy-SEGPHOS | 285(dec.) | +0.8(CH$_2$Cl$_2$) (c = 1.0) | −11.46(s) (CDCl$_3$) | |

One enantiomer of the compound specified with the words of 'HPLC separation' in the sixth column was isolated by HPLC with a preparative chiral column, which was SUMICHIRAL OA-3100 (20mm×250mm, 5m).

Abbreviations written in the second column represent the following compounds.

DMM-SEGPHOSO$_2$ : ((5,6), (5',6')-Bis(methylenedioxy) biphenyl-2,2'-diyl)bis(bis(3,5-dimethyl-4-methoxyphenyl)phosphine oxide)

DMM-SEGPHOS : ((5,6),(5',6')-Bis(methylenedioxy) biphenyl-2,2'-diyl)bis(bis(3,5-dimethyl-4-methoxyphenyl)phosphine)

DTBM-SEGPHOSO$_2$: ((5,6), (5',6') -Bis (methylenedioxy) biphenyl-2,2'-diyl)bis(bis (3,5-di-t-butyl-4-methoxyphenyl)phosphine oxide)

DTBM-SEGPHOS ((5,6),(5',6')-Bis(methylenedioxy) biphenyl-2,2'-diyl)bis(bis(3,5-di-t-butyl-4-methoxyphenyl)phosphine)

DTB-SEGPHOSO$_2$ : ((5,6), (5',6') -Bis(methylenedioxy) biphenyl-2,2'-diyl)bis(bis(3,5-di-t-butylphenyl) phosphine oxide)

DTB-SEGPHOS : ((5,6),(5',6')-Bis(methylenedioxy) biphenyl-2,2'diyl)bis(bis(3,5-di-t-butyl-phenyl) phosphine)

T-SEGPHOSO$_2$ : ((5,6), (5',6')-Bis(methylenedioxy) biphenyl-2,2'diyl)bis(bis(4-methylphenyl)phosphine oxide)

T-SEGPHOS : ((5,6),(5',6')-Bis(methylenedioxy)biphenyl-2,2'-diyl)bis(bis(4-methylphenyl)phosphine)

TB-SEGPHOSO$_2$ : ((5,6), (5',6')-Bis(methylenedioxy) biphenyl-2,2'-diyl)bis(bis(4-t-butylphenyl)phosphine oxide)

TB-SEGPHOS : ((5,6),(5',6')-Bis(methylenedioxy) biphenyl-2,2'diyl)bis(bis(4-t-butylphenyl)phosphine)

p-MeO-SEGPHOSO$_2$ : ((5,6), (5',6') -Bis(methylenedioxy) biphenyl-2,2'-diyl)bis(bis(4-methoxyphenyl)phosphine oxide)

p-MeO-SEGPHOS : ((5,6),(5',6')-Bis(methylenedioxy) biphenyl-2,2'-diyl)bis(bis(4-methoxyphenyl)phosphine)

p-Cl-SEGPHOSO$_2$ : ((5,6), (5',6')-Bis(methylenedioxy) biphenyl-2,2'-diyl)bis(bis(4-chlorophenyl)phosphine oxide)

p-Cl-SEGPHOS : ((5,6),(5',6')-Bis(methylenedioxy) biphenyl-2,2'-diyl)bis(bis(4-chlorophenyl)phosphine)

Cy-SEGPHOSO$_2$ : ((5,6), (5',6')-Bis(methylenedioxy) biphenyl-2,2'-diyl)bis(bis (cyclohexyl)phosphine oxide)

Cy-SEGPHOS : ((5,6),(5',6')-Bis(methylenedioxy) biphenyl-2,2'-diyl)bis(bis (cyclohexyl)phosphine)

mp : 246°–248° C.

1H-NMR(CDC13) : d 2.09(12H,d,J=0.5 Hz)

Example 36

Preparation of [RuI(p-cymene)((−)-DM-SEGPHOS)]I

A mixture of [Ru(p-cymene)I$_2$]$_2$ (67.4 mg, 0.069 mmol), (−)-DM-SEGPHOS (100.0 mg, 0.138 mmol), 3 ml of methylene chloride and 3 ml of ethanol was stirred in a 20 ml schlenk tube at 50 ° C. for 3 hours. The solvent was distilled off, followed by vacuum-drying to obtain 167.4 mg of the titled compound.

mp : 246°–248° C.

$^1$H-NMR(CDCl$_3$) : δ 2.09(12H,d,J=0.5 Hz), 2.16(12H,d, J=0.5 Hz),5.19(2H,d,J=1.6 Hz),5.72(2H,d,J=1.6 Hz), 6.56(2H,dd,J=8.0,3.3 Hz), 6.67(6H,m), 6.76(2H,m) , 6.81–6.83(6H,m)

$^{31}$P-NMR(CDCl$_3$) : δ−12.9

CI-MS m/z 722(M$^+$)

$[\alpha]_D^{24}$−114.7°(C 0.095, CHCl$_3$)

Example 37

Preparation of [Rh(cod)((−)-DM-SEGPHOS)]ClO4

A mixture of [Rh(cod)2]ClO4 (43.0 mg, 0.10 mmol), (−)-DM-SEGPHOS (73.0 mg, 0.10 mmol), 2 ml of methylene chloride and 2 ml of THF was stirred in a 20 ml schlenk tube at room temperature for 15 hours. The solvent was distilled off under reduced pressure, followed by vacuum-drying to obtain 103.3 mg of the titled compound.

$^{31}$P-NMR(CDCl$_3$) : δ 24.5(s), 25.4(s)

Use Example 1

Asymmetric hydrogenation of 2-oxo-1-propanol

A mixture of 44.8 mg (0.160 mmol) of [Ru(COD)Cl$_2$]$_2$, 100 mg (0.164 mmol) of (-)-SEGPHOS, 0.12 ml (0.86 mmol) of triethylamine and 5 ml of toluene was heated at reflux for 15 hours under a nitrogen stream. The solvent was distilled off under reduced pressure, followed by vacuum-drying. The resultant Ru$_2$Cl$_4$ [(-) -SEGPHOS]$_2$NEt$_3$ (11.2 mg, 0.0067 mmol), 2-oxo-1-propanol (3.0 g, 0.041 mol) and 6 ml of methanol were placed into a stainless autoclave, followed by heating with stirring at a hydrogen pressure of 10 atm at 65° C. for 16 hours. The reaction mixture was measured by GLC and was found to have a conversion rate of 99.8% and 97.4%ee.

Conversion was determined to be 99.8% by using FFAP (25 m×0.35 mm, I.D. 2.5 mm) according to a conventional method and optical purity was determined to be 97.4%ee by using α-DEX120™ (30 m×0.25 mm×0.25 μm) according to a conventional method.

Use Example 2

The asymmetric hydrogenation of methyl 2-benzamidemethyl-3-oxobutyrate

Methyl 2-benzamidemethyl-3-oxobutyrate (4.98 g, 20 mmol), [RuI(p-cymene) ((+)-DM-SEGPHOS]I (12.1 mg, 0.01 mmol), 17.5 ml of methylene chloride and 2.5 ml of methanol were placed into a stainless autoclave, followed by stirring at a hydrogen pressure of 10 atm at 70° C. for 20 hours. Conversion and diastereomeric excess were determined by HPLC analysis to be 98.5% and 93.3%de. Optical purity was determined by HPLC analysis to be 99%ee as Mosher's ester derived from an optically active α-methoxy-α-trifluoromethylphenyl acetyl chloride and the alcohol obtained.

What is claimed is:

1. A diphosphine compound of the formula (1):

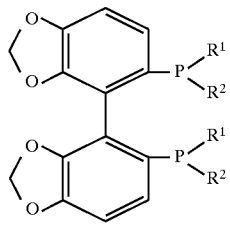

(1)

where R$^1$ and R$^2$ independently represent cycloalkyl, unsubstituted or substituted phenyl, or a five-membered heteroaromatic ring residue.

2. A diphosphine compound of the formula (2):

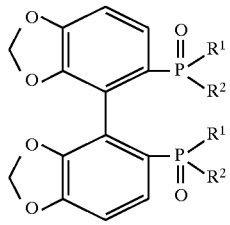

(2)

where R$^1$ and R$^2$ independently represent cycloalkyl, unsubstituted or substituted phenyl, or a five-membered heteroaromatic ring residue.

3. Phosphine oxide of the formula (3):

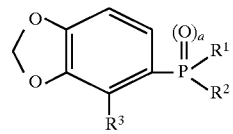

(3)

where R$^1$ and R$^2$ represent independently cycloalkyl, unsubstituted or substituted phenyl, or a five-membered heteroaromatic ring residue; R$^3$ represents hydrogen or halogen, and a represents 0 or 1.

4. A transition metal complex comprising a complex selected from rhodium complex, ruthenium complex, iridium complex, palladium complex and nickel complex, wherein said complex has as a ligand an optically active as compound defined in claim 1.

5. A transition metal complex of the formula (4):

$$MmLnXpSq \qquad (4)$$

where M represents a transition metal selected from rhodium, ruthenium, iridium, palladium and nickel, L represents an optically active diphosphine compound as defined in claim 1, and X and S are defined as follows:

when M=Rh, then X=Cl, Br, I, m=n=p=2, q=0;

when M=Ru, then m=n=1, X=OAc, m=n=1, p=2, q=0,
  or X=Cl, S=NEt$_3$, m=n=2, p=4, q=1,
  or X=methylallyl, m=n=1, p=2, q=0;

when M=Ir, then X=Cl, Br, I, m=n=p=2, q=0;

when M=Pd, then X=Cl, m=n=1, p=2, q=0,
  or X=II-allyl, m=n=p=2, p=0; and when M=Ni, then X=Cl, Br, I, m=n=1, p=2, q=0, where Ac is acetyl.

6. A catalyst comprising a transition metal complex of the formula (5):

$$[MmLnXpSq]Yr \qquad (5)$$

where M represents a transition metal selected from rhodium, ruthenium, iridium, palladium and nickel, L represents an optically active diphosphine compound as defined in claim 1, and X, S and Y are defined as follows:

when M=Rh, then X=cod, nbd, Y=Bf$_4$, ClO$_4$, PF$_6$, BPh$_4$, m=n=p=r=1, q=0;

when M=Ru, then X=Cl, Br, I, S=benzene, p-cymene, Y=Cl, Br, I, m=n=p=q=r=1,
  or Y=BF$_4$, ClO$_4$, PF$_6$, BPh$_4$, m=n=1, p=q=0, r=2;

when M=Ir, then X=cod, nbd, Y=BF$_4$, ClO$_4$, PF$_6$, BPh$_4$, m=n=r=1, p=1, q=0; and when M=Pd, then Y=BF$_4$, ClO$_4$, PF$_6$, BPh$_4$, m=n=r=1, p=q=0, where cod represents 1,5-cyclooctadiene, nbd represents norbornadiene, and Ph represents phenyl.

7. A catalyst for asymmetric hydrogenation comprising the transition metal complex according to claim 4.

* * * * *